United States Patent
Walter et al.

[11] Patent Number: 6,090,936
[45] Date of Patent: Jul. 18, 2000

[54] DEVICE FOR ISOLATING NUCLEIC ACIDS

[75] Inventors: Thomas Walter, Bichl; Michael Fritz, Biblis; Herbert Harttig, Altrip; Hans Lange, Lampertheim; Rolf Lerch, Ilvesheim, all of Germany

[73] Assignee: Boehringer Mannheim GmbH, Germany

[21] Appl. No.: 09/251,151

[22] Filed: Feb. 17, 1999

Related U.S. Application Data

[62] Division of application No. 08/617,696, Apr. 1, 1996, Pat. No. 5,910,246.

[30] Foreign Application Priority Data

Apr. 1, 1995 [DE] Germany .......................... 195 12 369

[51] Int. Cl.⁷ .......................... C07H 21/00; G01N 15/06
[52] U.S. Cl. .......................... 536/25.4; 422/50; 422/56; 422/57; 422/58; 422/68.1; 422/69; 422/211; 422/240; 435/6; 435/283.1; 435/289.1; 435/304.2
[58] Field of Search ................ 422/50, 68.1, 56, 422/57, 58, 69, 211, 240; 435/6, 283.1, 289.1, 304.2; 536/25.4

[56] References Cited

U.S. PATENT DOCUMENTS

| | | | |
|---|---|---|---|
| 4,522,713 | 6/1985 | Nussbaumer et al. | 210/136 |
| 4,573,900 | 3/1986 | Smith | 425/157 |
| 5,100,775 | 3/1992 | Smyczek et al. | 435/6 |
| 5,208,161 | 5/1993 | Saunders et al. | 210/232 |
| 5,264,184 | 11/1993 | Aysta et al. | 422/101 |

FOREIGN PATENT DOCUMENTS

| | | |
|---|---|---|
| 41 27 276 A1 | 9/1992 | Germany . |
| 673 679 A1 | 3/1995 | Germany . |
| 0 676 643 A3 | 4/1995 | Germany . |
| 0 687 502 A3 | 12/1995 | Germany . |
| WO 91/07648 | 5/1991 | WIPO . |
| WO 93/11218 | 6/1993 | WIPO . |

OTHER PUBLICATIONS

Vogelstein et al., Preparative and analytical purificatio of DNA from agarose, Proc. Nat'l. Acad. Sci. USA, vol. 76, No. 2, pp. 615–619, Feb. 1979.

Jakobi et al. Filter–Supported Preparation of λ Phage DNA, Institute of Experimental Pathology, German Cancer Research Center, Analytical Biochemistry 175, 196–201 (1988).

Japanese Unexamined Patent Publication No. 58899/1992 (Translation–in–part).

Japanese Unexamined Patent Publication No. 158144/1988 (Translation–in–part).

*Primary Examiner*—Ardin H. Marschel
*Attorney, Agent, or Firm*—Arent Fox Kintner Plotkin & Kahn, PLLC

[57] ABSTRACT

Device for the isolation of nucleic acids from a liquid sample by introducing the liquid into the device through an inlet opening and passage of the sample through a nucleic acid binding material and discharging of the resulting liquid through an outlet opening, wherein the nucleic acid binding material is inserted through the outlet opening during the manufacture of the device and the outlet opening is narrowed in order to hold the material. The device is particularly simple and reliable to manufacture but yet ensures that nucleic acids can be isolated without contamination.

12 Claims, 3 Drawing Sheets

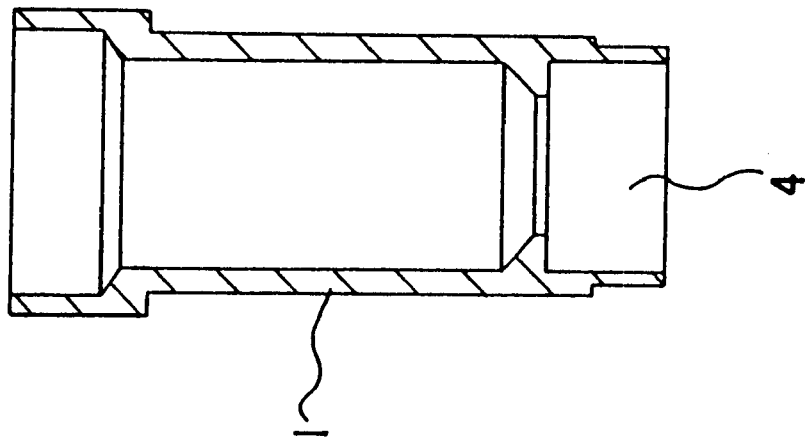
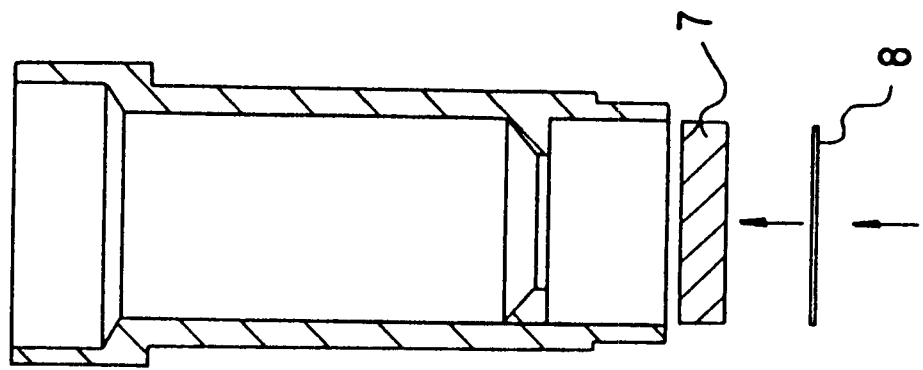
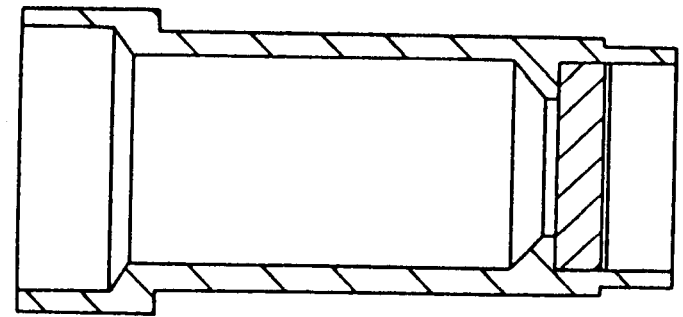
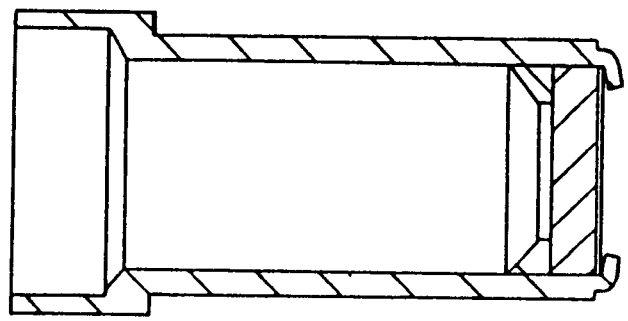

FIG.5
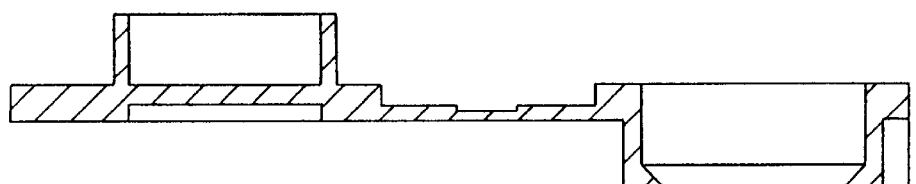
FIG.7
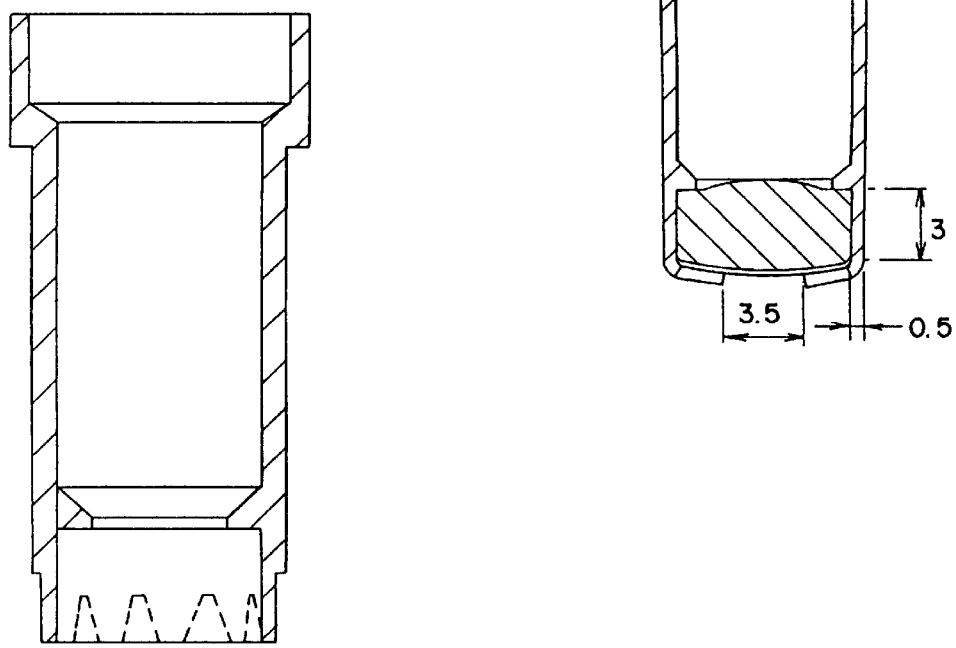
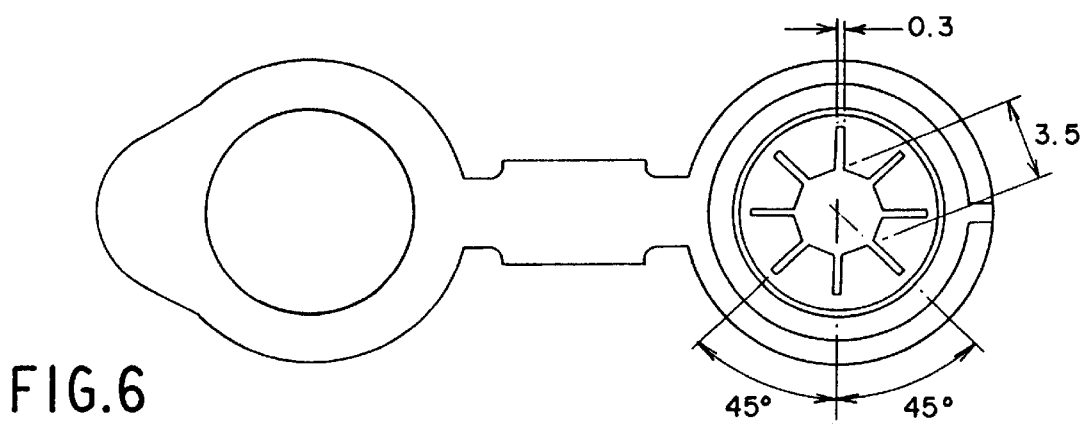
FIG.6

DEVICE FOR ISOLATING NUCLEIC ACIDS

This application is a divisional of application Ser. No. 08/617,696, filed Apr. 1, 1996, now U.S. Pat. No. 5,910,246.

The invention concerns a device for isolating nucleic acids, a process for manufacturing this device and a process for isolating nucleic acids with the aid of this device.

Recently nucleic acids have become more and more accepted as analytes in chemical methods of detection since they allow a very specific diagnosis of diseases. Thus for example the analysis of nucleic acid sequences enables a highly differentiated detection of viral or bacterial infections or the determination of a genetic disposition for a disease. This has been made possible by, among others, the introduction of amplification methods for nucleic acids. Nevertheless the amounts of nucleic acids available in a sample are quite small compared to other components of the sample liquid. Many of these components can interfere with the determination of nucleic acids. For this reason it has proven to be expedient to separate the nucleic acids from the majority of the components contained in a sample before carrying out the actual detection method.

At an early stage the adsorption of nucleic acids to solid phases was already suggested for this purpose. Thus for example the property of nucleic acids to bind to glass surfaces in the presence of chaotropic salts was described in Proc. Natl. Acad. Sci. USA 76, 615–619 (1979). In this case ground flint glass was used to isolate nucleic acid fragments from agarose gels in combination with a saturated solution of NaI to dissolve the agarose matrix. In this process more than 95% of the nucleic acids were bound after 2 hours at 25° C. whereby ca. 1 $\mu$g DNA/mg glass particles was bound. Subsequently the glass particles were washed several times and afterwards the nucleic acids were eluted. The resulting time requirement for this series of steps was at least 3 hours.

Alternative methods for purifying nucleic acids on glass surfaces were developed to improve the handling and shorten the time required. WO 91/07648 describes a cylindrical plastic vessel which contains a plastic membrane at the bottom which can also contain glass fibres. Several washing and elution steps are also necessary in this case. A similar process is also described in DE-A-4127276 in which the solutions containing nucleic acids are only in contact with the glass fibre surface for a short period. Corresponding products are obtainable from the said patent applicants. In the first case 50 ng to 30 $\mu$g is stated as the binding capacity with a size distribution of 100 to 23,000 bp. The yield is stated as 60 to 85%. In order to achieve maximum efficiency the manufacturer recommends that the sample be passed through at least twice since otherwise the yield is reduced by at least 25%. The yield for fragments having a size of more than 23,000 bp is at most 40%.

The centrifuge tubes that are provided each contain several layers of glass fibre fleece depending on the required binding capacity in a vessel with a highly conical bottom. A small outlet opening is located in the bottom. The centrifuge tubes are manufactured by firstly introducing the glass fibre fleece from above into the vessel and pressing it onto the bottom. Subsequently a ring is inserted into the vessel through the same opening, through which later the nucleic acid solution is applied, which by contact with the inner wall of the vessel presses the glass fibre fleece firmly onto the bottom and thus prevents the fleece from floating up during incubation with the sample containing nucleic acid. This type of centrifuge tube design has, as has now been established, the disadvantage that many interfering sample components are retained in it so that several washing steps are necessary for their complete removal. This in turn leads to a reduced yield of nucleic acids or to interference of subsequent enzymatic reactions. A binding capacity of 5 $\mu$g with 90% yield is stated for a 100 bp long fragment for a product that is available on the market. In a further product a yield of 75 to 90% with a binding capacity of 20 $\mu$g is achieved.

In the previously mentioned state of the art only the isolation of DNA but not the isolation of total nucleic acids or RNA is described.

The object of the invention was therefore to improve the products for isolating nucleic acids as well as their manufacture.

This object is achieved by a device for isolating nucleic acids from a liquid sample with an inlet and an outlet opening and a material for binding the nucleic acids located between these openings in which the outlet opening was narrowed after inserting the material. The vessel according to the invention may have almost any desired external shape. However, it preferably has an essentially cylindrical or, at least in parts, conical shape. A particularly preferred embodiment of this vessel has the shape of a tube e.g. of a conventional centrifuge tube. Such centrifuge tubes have a length of ca. 25 mm and a diameter of ca. 8.5 mm. This tube preferably has a component facing the inlet opening which is shaped to receive the sample containing nucleic acid. In particular the volume of this space is large enough to completely hold the sample. Additional structural elements can be provided at the inlet opening which enable the inlet opening to be closed by a cap. Such constructions are also known as Eppendorf caps.

The material for binding the nucleic acids is preferably located in the zone of the device which is near to the outlet opening. This means that the space in the tube which is located between the material and the outlet opening should preferably be kept small in order to reduce the risk of retaining liquid droplets and thus of reducing the risk of contamination. The material for binding nucleic acids is fixed in the device. For this purpose a holding device which cannot be removed without destroying the device is provided in the direction of the inlet opening. It is preferably made of the same material as the vessel. In this embodiment the device is particularly advantageous since the vessel according to the invention including the holding device can then be manufactured in an injection moulding process. The holding device preferably protrudes from the inner wall of the vessel into the inner space and is bevelled in the direction of the inlet opening. These requirements can for example be achieved by a circumferential rim or projection in the inner space. The bevelling towards the inlet opening ensures that only obtuse angles result in the inner space. A major disadvantage of the known vessels has namely proven to be that liquids such as the sample liquid are retained in right angles or more acute angles and also if a ring does not lie perfectly against the inner wall of the vessel thus reducing the efficiency of the washing steps. Moreover a relatively critical process step, namely the insertion of the ring, is saved in the manufacture of this vessel. The provision of the holding device already during the manufacture of the vessel furthermore enables more flexibility in the choice of holding devices and can therefore avoid the meeting of structural components at acute angles.

However, the holding devices may also be non-circumferential structural components e.g. protrusions arranged regularly or irregularly on a comparable level. Materials for binding nucleic acids are known. Materials with a surface made of glass are particularly preferred as the material. This material is particularly preferably used in the form of a fleece since fleeces can very simply be fitted into the shape of the inner wall of the device according to the invention without a major change in this outer form resulting while the material is being used to isolate nucleic acids. In addition fleeces are readily permeable to liquids. Fleeces with a thickness between 40 and 100 mg/ccm (g/cdm) have proven to be particularly preferable.

In a preferred embodiment the nucleic acid binding material is supported over its whole area by a liquid-permeable porous matrix towards the outlet opening. This matrix is referred to as a supporting fleece in the following. Such a liquid-permeable matrix is for example a fleece made of materials which are relatively inert towards the components of the liquid and bind as few components as possible or are those which bind nucleic acids. In this case polyester or polypropylene have proven to be particularly preferable. This matrix separates the nucleic acid binding material preferably almost completely (i.e. by more than 90%) from the outlet opening so that no liquid can flow from the nucleic acid binding material directly into the outlet opening. This matrix has two functions. Firstly it serves to retain fibres of the nucleic acid binding material which may not be firmly anchored (improvement in yield). Moreover this matrix enables the outlet opening of the vessel to firstly be kept wide enough to enable the insertion of the nucleic acid binding material through it into the vessel and subsequently the outlet opening can be narrowed. If the nucleic acid binding material is made of a particulate matrix, this material is supported by a liquid-permeable porous matrix also on the side of the inlet opening in order to avoid a whirling up of the material into the sample holding space.

A feature of the device according to the invention is that the outlet opening is narrowed after introducing the nucleic acid binding material. The outlet opening is preferably narrowed to such an extent that the nucleic acid binding material and the supporting matrix cannot escape from the outlet opening. The more rigid the material or the matrix is, the less pronounced does the constriction have to be. The constriction is preferably a rim which extends inwards around the circumference of the tube wall so that for example in the case of a tube diameter of 8 mm, the rim protrudes into the tube interior from each side by at least 0.5 mm, preferably between 0.75 and 1.5 mm. The lower limit of the protrusion is limited by the retention of the material and the matrix whereas the upper limit is limited by the as completely as possible aspiration of the fleece through the outlet opening.

The invention in addition concerns a process for manufacturing a vessel for isolating nucleic acids from a liquid sample with an inlet and an outlet opening and a material for binding the nucleic acids located between these openings by inserting the material through the outlet opening towards the inlet opening up to a holding device mounted in the vessel and narrowing the outlet opening so that the material is retained between the holding device and the site of constriction. The constriction can for example be achieved by flanging e.g. thermally or by thermal fixing. This manufacturing process is particularly simple and particularly reliable with regard to fixing the material.

The vessel according to the invention is preferably made of material capable of injection moulding e.g. polyethylene, polypropylene, polycarbonate or polyurethane, polypropylene is particularly preferred.

A subject matter of the invention is also the use of the material according to the invention to isolate nucleic acids in particular a method for isolating nucleic acids from a liquid sample by introducing the sample into the vessel according to the invention through an inlet opening, passage of the sample through the material and abolition of the binding of the nucleic acid to the material.

In a typical method the sample is introduced by pipetting a desired amount of sample liquid into the vessel. Afterwards the sample is passed through the material. This can for example be achieved by centrifugation in which case the liquid is spun out of the vessel through the material and the outlet opening. In this process the nucleic acids are immobilized on the matrix whereas the remaining sample liquid is discharged. The matrix is preferably subsequently washed once with a washing buffer of a medium salt content by which means residual sample liquid and components which are not to be isolated are removed from the material.

Afterwards the nucleic acids immobilized on the matrix can be eluted by a low salt buffer. Such buffers are known from DE 3724442 and Analytical Biochem. 175, 196–201 (1988). A buffer with a low salt content that is less than 200 mM NaCl is preferably used e.g. 10 mM Tris-HCl, 1 mM EDTA, pH 8.0 or $H_2O$. Relatively high yields are achieved with the matrix according to the invention.

BRIEF DESCRIPTION OF THE DRAWINGS

A cross-section of a particularly suitable vessel according to the invention is shown in FIG. 1.

The vessel according to the invention that is shown is composed of an essentially cylindrical part 1 which has an inlet opening 2 at one end which can be closed with a cap 3. Towards the outlet opening 4 there are holding devices 5 the bevelling 6 of which can be clearly seen. In the preferred embodiment the holding devices are a circumferential rim made of the same material as the cylindrical body 1. The nucleic acid binding material 7 border on the holding devices. The material is separated from the outlet opening 4 by a supporting fleece 8. The supporting fleece is secured within the vessel by the rim 9.

FIG. 2 shows a tube before being equipped with the nucleic acid binding material.

FIGS. 3A and 3B show the equipping of the tube with the nucleic acid binding material 7 and a supporting fleece 8.

FIG. 4 shows the final tube according to the invention.

FIG. 5 shows a tube whose flange edge has a slit (longitudinal section, dimensions in mm).

FIG. 6 shows the tube of FIG. 5 from below.

FIG. 7 shows the tube of FIG. 5 analogously to FIG. 3A in a state before flanging the rim. The slits are drawn with a dotted line.

Figure 1:
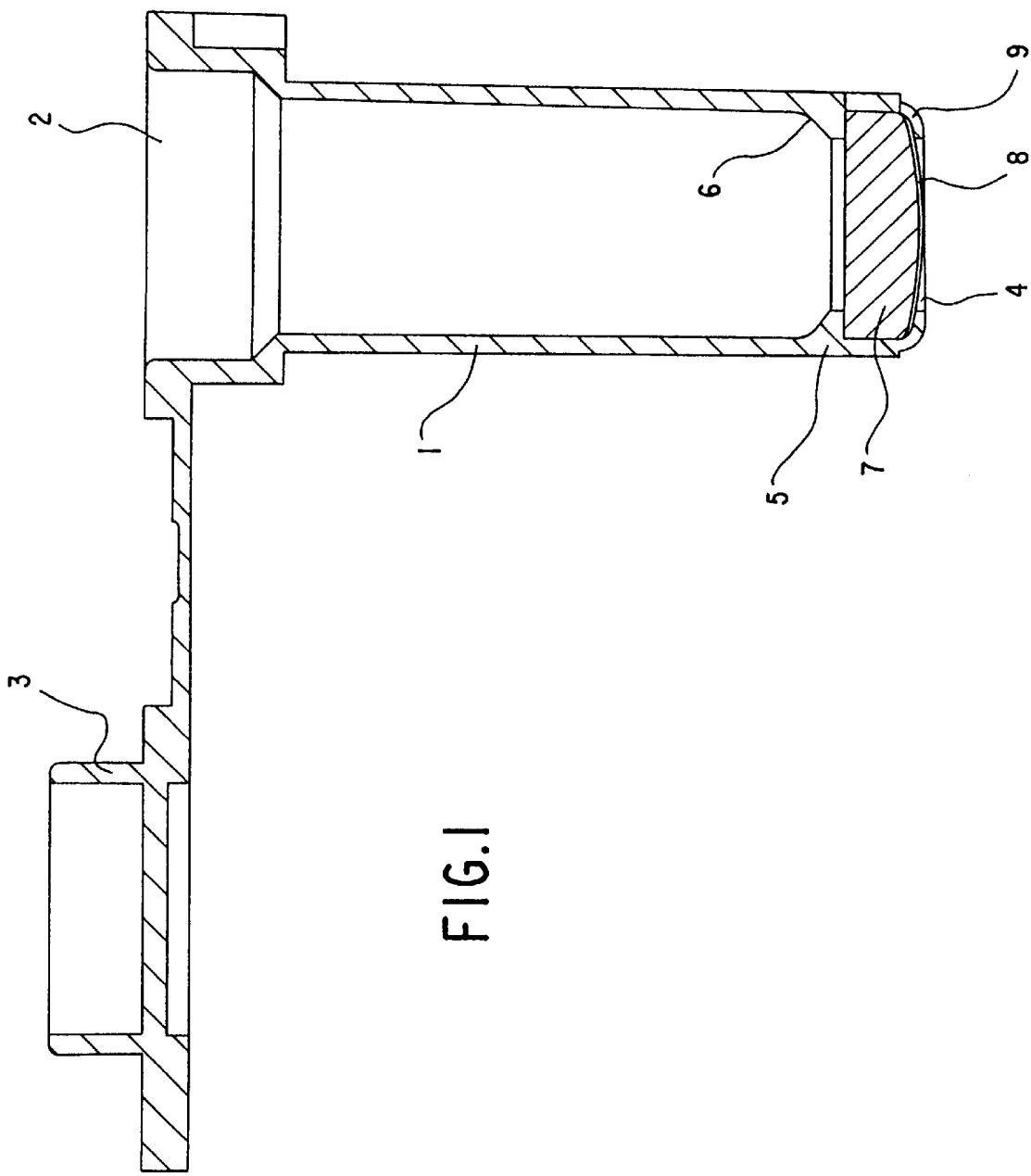

The invention is further elucidated by the following examples:

EXAMPLE 1

Manufacture of a Centrifuge Tube According to the Invention

The basic body 1 of a centrifuge tube shown in longitudinal section in FIG. 2 which has a length of ca. 25 mm and a diameter of ca. 8.5 mm is manufactured in an injection moulding process from polypropylene PPN 1060 "natur". One glass fibre fleece (WF 264 Whatman, area weight 60 g/m$^2$) 7 and a supporting fleece 8 are inserted into the injection moulding machine and punched out. Depending on the desired binding capacity several glass fleeces 7 are used e.g. 7 pieces. The punched out fleeces are inserted into the centrifuge tube from the outlet opening side as shown FIGS.

3A and 3B. Afterwards the outlet opening 4 is narrowed by reshaping the warm plastic that is still about 60° C. warm with a die to such an extent that both fleeces are fixed firmly as shown in FIG. 4.

EXAMPLE 2

Isolation of Plasmid DNA from E. coli Cultures
Culture of E. coli×pUC19

25 ml LB-medium+ampicillin (150 μg/ml) were inoculated with a single colony and incubated overnight at 37° C. while shaking. The $OD_{600}$ measurement yielded a value of 2.0 (corresponding to ca. $2 \times 10^9$ cells/ml). Various E. coli strains were used.

Isolation of the Plasmid DNA 1.5 ml of the bacterial culture is transferred into an Eppendorf reaction vessel and centrifuged for ca. 30 seconds at maximum speed in an Eppendorf bench centrifuge type 5415C. The supernatant is removed, the sediment is completely resuspended in 250 μl buffer I (50 mM Tris-HCl, 10 mM EDTA, 100 mg/ml RNase A, pH 8.0) and carefully admixed with 250 μl buffer II (0.2 M NaOH, 1% sodium dodecylsulfate). The cells lyse completely and yield in a clear solution. The mixture is mixed with 350 μl buffer III (2.9 M guanidinium HCl, 0.65 M K acetate, pH 4.15) and incubated for ca. 3 min on ice. A white precipitate is formed which is sedimented by centrifugation, a filter tube is inserted into a receiving vessel and the supernatant is applied to the filter tube. The liquid is transferred through the glass fleece by centrifugation. The eluate is discarded and 500 μl washing buffer I (5 M guanidinium HCl, 20 mM Tris, 37% ethanol, pH 6.65) is applied and centrifuged. The use of washing buffer I is optional for particularly nuclease-rich E. coli strains. Subsequently 500 μl washing buffer II (20 mM NaCl, 2 mM Tris, 80% ethanol, pH 7.5) is applied to the filter tube and centrifuged as before. The filter tube is now transferred into a new Eppendorf reaction vessel and plasmid DNA is eluted in 100 ml TE (10 mM Tris-HCl, 0.1 mM EDTA, pH 8.5).

Table 1 shows the yield and purity of the isolated plasmid DNA:

TABLE 1

Yield and purity of isolated plasmid DNA from various E. coli strains

| Strain | Washing buffer I | Washing buffer II | Yield [μg] | $OD_{260}/OD_{280}$ |
|---|---|---|---|---|
| XL 1 blue | yes | yes | 8.9 | 1.8 |
| XL 1 blue | no | yes | 9.4 | 1.82 |
| DH5α | yes | yes | 4.2 | 1.52 |
| DH5α | no | yes | 4.2 | 1.62 |
| HB101 | yes | yes | 4.7 | 1.7 |
| HB101 | no | yes | 5.8 | 1.77 |

EXAMPLE 3

Purification of Reaction Products of the Polymerase Chain Reaction (PCR)

Separation Properties of the Filter Tube

10 μg molecular weight standard VIII (Boehringer Mannheim, fragment length [bp]: 1114, 900, 692, 501, 489, 404, 320, 242, 190, 147, 124, 110, 67, 37, 34, 26, 19) in 100 μl TE is admixed with bovine serum albumin (20 mg/ml). 500 μl NA binding buffer (3 M guanidinium thiocyanate, 10 mM Tris-HCl, 5% ethanol (v/v), pH 6.6, 25° C.) is added to this mixture and carefully mixed. The solution is applied to a filter tube and centrifuged for ca. 30 seconds in an Eppendorf bench centrifuge type 5415C. The filtrate is collected, it can be stored for later analyses. The fleece is washed with 500 μl washing buffer II and subsequently dried by a short centrifugation. The bound nucleic acid is eluted with 50 μl TE.

Gel Electrophoresis and Silver Staining

A polyacrylamide gel electrophoresis using the Phast system (Pharmacia) is carried out to check the separation of the model protein BSA and smaller DNA fragments.

4 μl of the eluate is admixed with 1 μl 5×sample buffer. 4 μl length standard VIII and 4 μl of a 1:100 dilution of the BSA solution in TE buffer also admixed with 1 μl 5×sample buffer are used as control.

The samples are briefly centrifuged in an Eppendorf centrifuge and 3 μl of the samples are applied to a 6/4 comb (Pharmacia) and separated in a Phast gel, gradient 8–25% (Pharmacia) using native buffer strips (Pharmacia).

Subsequently the samples are detected in the Phast system development unit (Pharmacia) by silver staining.

Evaluation

The individual DNA fragments from the eluate are separated according to the control length standard VIII. The fragments <100 bp in the eluate have been separated by purification with the filter tube. In addition no protein band corresponding to the BSA control lane is visible.

Phast gel separation program:

| | | | | | |
|---|---|---|---|---|---|
| 1) Preliminary run | 400 V | 10 mA | 2.5 W | 15° C. | 100 Vh |
| 2) Application | 400 V | 1 mA | 2.5 W | 15° C. | 5 Vh |
| 3) Separation | 400 V | 10 mA | 2.5 W | 15° C. | 45 Vh |

After separation the gels are incubated for 5 minutes in 25% trichloroacetic acid solution.

| Phase gel development program | | | |
|---|---|---|---|
| 1) | 5% glutaraldehyde | 5 minutes | 50° C. |
| 2) | $H_2O$ | 2 minutes | 50° C. |
| 3) | $H_2O$ | 2 minutes | 50° C. |
| 4) | 0.4% $AgNO_3$ | 10 minutes | 40° C. |
| 5) | $H_2O$ | 0.5 minutes | 30° C. |
| 6) | $H_2O$ | 2.5 minutes | 30° C. |
| 7) | $NaHCO_3$/formaldehyde | 0.5 minutes | 30° C. |
| 8) | $NaHCO_3$/formaldehyde | 4 minutes | 30° C. |
| 9) | 10% ethanol/5% acetic acid | 2 minutes | 50° C. |
| 10) | 5% glycerol/10% acetic acid | 3 minutes | 50° C. |

Purification of PCR Reaction Products

DNA of the phage lambda is used as a matrix for the production of PCR products of the following lengths: 500 bp, 750 bp, 1500 bp, 3000 bp. The following PCR preparations are pipetted together, mixed and incubated in a Perkin-Elmer type 9600 thermocycler.

| Length of PCR product [bp] | 500 | 750 | 1500 | 3000 |
|---|---|---|---|---|
| $H_2O$ | 372.5 μl | 372.5 μl | 372.5 μl | 372.5 μl |
| dNTP [10 mM] | 40 μl | 40 μl | 40 μl | 40 μl |
| λ-DNA [1 ng/μl] | 25 μl | 25 μl | 25 μl | 25 μl |
| 10 × reaction buffer | 50 μl | 50 μl | 50 μl | 50 μl |
| primer 1 | 5 μl | 5 μl | 5 μl | 5 μl |
| primer 2 | 5 μl | | | |

-continued

| Length of PCR product [bp] | 500 | 750 | 1500 | 3000 |
|---|---|---|---|---|
| primer 3 | | 5 μl | | |
| primer 5 | | | 5 μl | |
| primer 7 | | | | 5 μl |
| primer 10 | | | | |
| taq polymerase [U] | 2.5 | 2.5 | 2.5 | 2.5 |

All reagents were from the Boehringer Mannheim PCR Core Kit (Cat. No. 1 578 553).

| Thermocycler program for 500, 750 and 1500 bp: | | 3000 bp: | |
|---|---|---|---|
| 2 min | 94° C. | 2 min | 94° C. |
| 10 cycles: | | 10 cycles: | |
| 10 sec. | 94° C. | 10 sec. | 94° C. |
| 30 sec. | 55° C. | 30 sec. | 55° C. |
| 1 min. | 72° C. | 5 min. | 72° C. |
| 20 cycles: | | 20 cycles: | |
| 10 sec. | 94° C. | 10 sec. | 94° C. |
| 30 sec. | 55° C. | 30 sec. | 55° C. |
| 1 min. | 72° C. + 20 sec./cycle | 5 min. | 72° C. + 20 sec./cycle |
| 7 min. | 72° C. | 7 min | 72° C. |

The PCR products were purified as described above and analysed in a Phast gel system. Parallel thereto one aliquot of the reaction product in each case was analysed before the purification.

Evaluation

Excess primers have been removed in all PCR products compared to before the purification. It was possible to isolate between 1.4 and 4 μg PCR product.

Cloning of PCR Products pUCIQ17 (3632 bp, Boehringer Mannheim) was linearized with the restriction enzyme DraII and amplified in the following PCR mixture:

| PCR mixture: | | PCR program (PE 9600) 18 cycles: | |
|---|---|---|---|
| pUCIQ17 | 10 ng | 10 sec. | 94° C. |
| primer 1 | 2 μM | 30 sec. | 57° C. |
| primer 2 | 2 μM | 4 min. | 72° C. |
| 10 × buffer | 50 μl | | |
| dNTP | 0.2 mM | | |
| Taq polymerase | 2.5 U | | |
| H₂O | ad 500 μl | | |

All reagents were from the Boehringer Mannheim PCR Core Kit.

The primers bind at the nucleotides 3500 and 3632 and yield a 3493 bp PCR product. They contain a cleavage site for the restriction enzyme ClaI, this cleavage site is not present in the plasmid pUKIQ17.

Primer 1: 5'-AGCTTATCGATGGCACTTTTCGGGGAAA TGTGCG-3' (SEQ ID NO. 1)

Primer 2: 5'-AGCTTATCGATAAGCGGATGCCGGGAG CAGACAAGC-3' (SEQ ID NO. 2)

The reaction product was purified according to the above-mentioned method following the PCR reaction. In comparison a purification was carried out by precipitation with polyethylene glycol precipitation (PEG) (Barnes, W. M. (1992) Gene 112, 29). Interfering components for the subsequent religation reaction are removed by this means. Both samples are cleaved with the restriction enzyme ClaI and separated over an agarose gel. The DNA fragments are eluted from the agarose gel. The methods used for this are standard methods and are for example described in Sambrook, J. Fritsch, E. F. & Maniatis, T. (1989) Molecular Cloning: A Laboratory Manual, 2nd edition, CSH Laboratory Press, Cold Spring Harbor, N.Y.

The samples (max. 30 ng) are religated according to the kit instructions using the Rapid DNA Ligation Kit (Boehringer Mannheim GmbH, Cat. No. 1 635 379) and transformed into competent E. coli DH5α cells. The cells are streaked out on TN Ap 100 X-Gal plates and incubated overnight at 37° C. The colonies are counted the next day, the result is shown in Table 2.

| Purification | Filter tube | PEG |
|---|---|---|
| Number of colonies | 2212 | 2832 |

The number of colonies is of the same order of magnitude when purifying by means of a filter tube as when purifying by means of PEG. Thus the filter tube method which is very much simpler yields a nucleic acid which is of comparable purity to that of the PEG method which is considerably more time-consuming.

EXAMPLE 4

Embodiment With a Slotted Flanged Rim and a Smaller Outlet Opening

In a further embodiment of the centrifuge tube according to the invention the outlet opening is much more constricted as shown in FIG. 5. In this embodiment the flanged rim of the outlet opening has slits (as shown in FIG. 6). Using this arrangement it is possible to centrifuge particularly highly viscous solutions without a large amount of residual liquid remaining in the device after the centrifugation.

EXAMPLE 5

The chosen embodiment of the centrifugation device according to the invention in example 1 and example 4 prevents liquid from remaining in dead spaces of the device after centrifugation. Incomplete centrifugation leads to a loss in yield and to a lower purity of the isolated nucleic acid.

Residual Liquid After Filling in 500 μl Water and Subsequent Centrifugation for 2 Minutes at 6000×g

| | | | | | | MV. |
|---|---|---|---|---|---|---|
| Centrifuge tube acc. to example 1 | 1.7 mg | 1.6 mg | 1.6 mg | 1.4 mg | 1.8 mg | 1.6 mg |
| QIA Quick Device | 9.5 mg | 9.9 mg | 9.9 mg | 10.2 mg | 10.5 mg | 10.0 mg |
| centrifuge tube acc. to example 4 | 1.7 mg | 2.0 mg | 1.5 mg | 2.3 mg | 2.1 mg | 1.9 mg |

MV: mean value

It can be seen that the tubes according to the invention retain significantly less residual liquid. This can in particular be attributed to the bevelling on the holding device.

---

---

We claim:

1. A device suitable for isolating a nucleic acid from a liquid sample, the device comprising:

a conduit having side walls which define a hollow interior, the conduit having an inlet opening and an outlet opening, wherein a slotted flanged rim is formed at the outlet opening; and a nucleic acid binding material located in the hollow interior, wherein the slotted flanged rim is configured to prevent the nucleic acid binding material from escaping through the outlet opening.

2. The device of claim 1, further comprising a holding means for fixing the nucleic acid binding material to the device.

3. The device of claim 2, wherein the holding means protrudes from the side walls into the hollow interior.

4. The device of claim 1, wherein the nucleic acid binding material is located adjacent the outlet opening.

5. The device of claim 1, wherein the nucleic acid binding material comprises a glass fleece.

6. The device of claim 5, wherein the glass fleece has a density of between 40 and 100 mg/ccm.

7. The device of claim 1, further comprising a liquid-permeable porous matrix located between the nucleic acid binding material and the outlet opening.

8. The device of claim 7, wherein the outlet opening has a given size, and the liquid-permeable porous matrix covers at least 90% of the given size.

9. The device of claim 2, wherein the holding means is configured such that it cannot be removed from the device without destroying the device.

10. The device of claim 2, wherein the conduit is comprised of a material capable of injection molding.

11. The device of claim 10, wherein the material is selected from the group consisting of polyethylene, polypropylene, polycarbonate and polyurethane.

12. A device suitable for isolating a nucleic acid from a liquid sample, the device comprising:

a conduit having side walls which define a hollow interior, the conduit having an inlet opening and an outlet opening, wherein a first slotted flanged rim is formed at the outlet opening;

a nucleic acid binding material located in the hollow interior, wherein the first slotted flanged rim prevents the nucleic acid binding material from escaping through the outlet opening; and a holding rim which fixes the nucleic acid binding material to the device, wherein the holding rim protrudes from the side walls into the hollow interior and is formed such that obtuse angles are formed between the side walls and the holding rim.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (xi) SEQUENCE DESCRIPTION: SEQ ID NO:1:

AGCTTATCGA TGGCACTTTT CGGGGAAATG TGCG           34

(2) INFORMATION FOR SEQ ID NO:2:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (xi) SEQUENCE DESCRIPTION: SEQ ID NO:2:

AGCTTATCGA TAAGCGGATG CCGGGAGCAG ACAAGC         36